United States Patent [19]

Kowalski

[11] 4,314,337

[45] Feb. 2, 1982

[54] METHOD OF AND APPARATUS FOR GENERATING IMPROVED RECONSTRUCTION IMAGES IN COMPUTERIZED TOMOGRAPHY EQUIPMENT

[75] Inventor: Günter Kowalski, Rellingen, Fed. Rep. of Germany

[73] Assignee: U.S. Philips Corporation, New York, N.Y.

[21] Appl. No.: 27,552

[22] Filed: Apr. 6, 1979

[30] Foreign Application Priority Data

Apr. 15, 1978 [DE] Fed. Rep. of Germany ....... 2816462

[51] Int. Cl.³ ............................................. G01N 23/00
[52] U.S. Cl. ................................. 364/414; 250/445 T
[58] Field of Search ..................... 364/414; 250/445 T

[56] References Cited

U.S. PATENT DOCUMENTS 3,983,399 9/1976 Cox, Jr. et al. ..................... 364/414
4,144,569 3/1979 Wagner ............................... 364/414
4,149,081 4/1979 Seppi .................................. 364/414

*Primary Examiner*—Errol A. Krass
*Attorney, Agent, or Firm*—Thomas A. Briody; Robert T. Mayer; Jack E. Haken

[57] ABSTRACT

The method relates to an X-ray apparatus, which by the rotary scanning with the aid of a fan-shaped radiation beam provides measuring data about the radiation attenuation in the layer of a body, from which subsequently the absorption distribution of the layer being examined is calculated. In such an apparatus it is important that the center of rotation is accurately known. If this center is not exactly known, this leads to blurring in the reconstructed image. If scanning is not performed over a full revolution, this moreover gives rise to streaking artefacts. The method proposed automatically yields the center of rotation from the measuring data, so that during the subsequent reconstruction allowance can be made for the center of rotation.

4 Claims, 3 Drawing Figures

METHOD OF AND APPARATUS FOR GENERATING IMPROVED RECONSTRUCTION IMAGES IN COMPUTERIZED TOMOGRAPHY EQUIPMENT

The invention relates to a method of determining a radiation absorption distribution in a plane of a body by means of computerized tomography. A plane of a body be irradiated with penetrating radiation (for example X-radiation) from different directions which extend in said plane, using a radiation source which emits a fan-shaped beam and which is rotatable about a centre. The attenuation of the radiation be measured by detectors, which supply measuring data by means of which the absorption distribution is determined. The invention furthermore relates to apparatus for carrying out the method.

BACKGROUND OF THE INVENTION

A method of the type mentioned in the preamble is described by G. Kowalski and W. Wagner in "OPTICA ACTA", 1977, Vol. 24, no. 4, pages 327–384. According to this method an X-ray source, whose radiation is collimated to a flat fan-shaped radiation beam which is incident on an array of adjacent detectors disposed in said plane is rotated about a centre of rotation together with said detector array, which supplies the measuring data which are a measure of the attenuation along individual radiation paths in such a way that the radiation beam irradiates the body slice to be examined in different directions. The size (width) of the measuring area of the individual detectors divides the radiation beam into separate subbeams, which in their turn define the shape and size of the radiation paths.

The absorption distribution of the irradiated body section can then be reconstructed as an image in known manner from the measuring data thus obtained.

However, the centre of rotation of the examination apparatus (radiation source detector array) should then be known exactly. If this centre is not known with sufficient accuracy, blurring in the reconstructed computerized tomography image results. Moreover, if the examination apparatus is not rotated through a full revolution lack of knowledge of the centre of rotation can also gives rise to streaking artefacts.

SUMMARY OF THE INVENTION

It is the object of the invention to provide a method which eliminates errors produced in the reconstructed computerized-tomography image as a result of the centre of rotation of an examination apparatus not being known with sufficient accuracy.

To this end a method according to the invention is characterized in that prior to the determination of the radiation absorption distribution a first intermediate value is determined for each detector, which value is proportional to an intermediate sum obtained by summation of the measuring data measured with the detector in the various directions and proportional to goniometric functions $k_m$, $l_m$, whose arguments are proportional to the difference between a variable detector number, which is representative of the position of a detector, and a fixed predetermined detector number, and to an angle enclosed by the centres of two adjacent detectors and the radiation source, after which the first intermediate values from all detectors are added so as to form a first sum, that furthermore for each detector a second intermediate value, which is proportional to the intermediate sum and the function $l_m$, is determined and all second intermediate values are added so as to obtain a second sum, after which for determining a third intermediate result the first sum is divided by the second sum, from which third intermediate result a correction value is derived, which is proportional to the third intermediate result and inversely proportional to the said angle, by means of which correction value, starting from the fixed predetermined detector number to which the correction value is added, a detector number is determined which is representative of the centre of rotation.

An embodiment of a method in accordance with the invention is characterized in that prior to the determination of the radiation absorption distribution for each direction of measurement a first intermediate value is determined by a summation of measuring data measured with the detectors in said direction and which are weighted with goniometric functions $k_m$, $l_m$ whose arguments are proportional to the difference between a variable detector number, which determines the position of the detector, and a fixed predetermined detector number, and to an angle which is enclosed by the connecting lines of the centres of two adjacent detectors and the radiation source, that the first intermediate values for all directions are added so as to form a first sum, that furthermore for each direction a second intermediate value is determined by summation of the measuring data which are measured by the detectors in said direction and which are weighted with the goniometric function $l_m$, and that all second intermediate values for all directions are added so as to obtain a second sum, after which for determining a third intermediate result the first sum is divided by the second sum, which third intermediate result yields a correction value which is proportional to the third intermediate result and inversely proportional to the said angle, from which, starting from the fixed predetermined detector number to which the correction value is added, a detector number of derived which is representative of the centre of rotation.

By determining the precise position of the centre of rotation of the examination apparatus it is achieved that the positions of the individual radiation paths relative to the centre of rotation of the examination apparatus can be determined accurately, so that the computerized-tomography image to be reconstructed, which is for example obtained by convolution and subsequent back-projection of the convolved measuring data along the relevant radiation path and by superposition, no longer exhibits image errors owing to the centre of rotation not being known with sufficient accuracy.

The centre of rotation is preferably determined with the aid of measuring data obtained by means of a phantom, because a phantom has the advantage that it cannot perform movements which give rise to errors. Once the centre of rotation has been determined this can be stored in a memory, so that it is available for a large number of subsequent examinations. However, it is alternatively possible to determine the centre of rotation again for each individual examination of a body.

An apparatus for carrying out the inventive method of determining the radiation absorption distribution in a plane of a body, comprises a radiation source for generating penetrating radiation, a plurality of detectors, arranged adjacent each other in the plane, for supplying measuring data which are a measure of the attenuation of the radiation which passes through the body in different directions in said plane, a data store for the storage of the measuring data measured by means of the detectors, which data store is connected to a computer for determining the radiation-absorption distribution in the plane by superposition of the measuring data and is characterized in that the detectors are connected to an adder circuit for the formation of an intermediate sum and all adder circuits are connected to a parallel-series converter, which under control of the computer renders the intermediate sums sequentially available on an output, the output of the parallel-series converter being connected both to an input of a first and to an input of a second multiplier, whose further inputs are respectively connected to outputs of a first and a second function generator, which are controlled by the computer, outputs of said multipliers each being connected to an adder circuit, whose outputs are applied to a dividing circuit, whose output in its turn is fed to an input of the computer, the first function generator generating a cosine function ($l_m$), whose argument is proportional to the value ($m - m_c$) supplied by the computer, the second function generator generating a product ($l_m \cdot k_m$) of a sine and cosine function, of which functions the arguments are equal and proportional to the value ($m - m_c$) supplied by the computer, and the sum of the products from the multipliers is applied to the dividing circuit, after all intermediate sums ($\tilde{Q}m$) have consecutively been applied to the multipliers.

DESCRIPTION OF THE DRAWINGS

The method and apparatus in accordance with the invention will now be described in more detail by way of example with reference to the drawing.

FIG. 1 shows an examination apparatus 1 comprising an X-ray source 2, whose radiation is collimated to a flat fan-shaped radiation beam (the collimators not being shown). The radiation beam 3 passes through a body to be examined 4 and reaches a detector array 5, comprising separate detectors $D_m$ which are disposed adjacent each other in the plane defined by the radiation beam 3. The index m designates the sequence number of the individual detectors $D_m$, and thus represent the position of a detector $D_m$ within the detector array 5. The individual detectors $D_m$ divide the radiation beam 3 into measuring beams 6 which define individual radiation paths, whose dimensions in the plane depends on the width b of the individual detectors $D_m$, each measuring beam 6 having a central ray 7.

Figure 1:
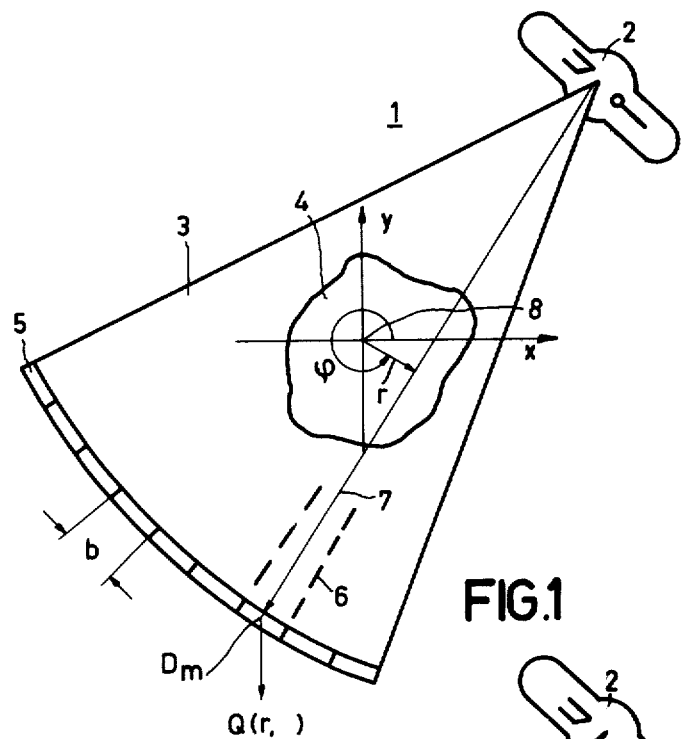
FIG. 1 schematically represents an examination apparatus.

A rectangular coordinate system (x,y) is situated within the plane irradiated by the beam 3. The origin of the coordinate system is also the origin of a polar coordinate system r, $\phi$, which is situated in the same plane and which is representative of the assumed position of the centre of rotation $r_c$ of the examination apparatus 1. The location of a relevant measuring beam 6 and thus that of the associated raddiation path is represented by the polar coordinates r and $\phi$ of the relevant central ray 7 when radius r is the perpendicular to the central ray 7.

The measuring data Q(r, $\phi$) are proportional to the line integral of the absorption coefficient along the associated radiation path of the relevant measuring beam 6.

In "OPTICA ACTA", 1977, vol. 24, No. 4, pages 327–348 G. Kowalski and W. Wagner state that the projection of the centre of gravity $r_p$ of the irradiated plane of the body 4 may be approximated by the equation $$r_p(\phi) = \frac{\int_{-r_{max}}^{r_{max}} Q(r,\phi) \, r \, dr}{\int_{-r_{max}}^{r_{max}} Q(r,\phi) \, dr} \quad (a)$$

this centre of gravity $r_p$ does not coincide with the centre of rotation $r_c$ it oscillates about the projection of the centre of rotation $r_c$, so that it may be obtained by averaging the centre of gravity $r_p$ with:

$$r_c = \frac{1}{2\pi} \int_0^{2\pi} r_p(\phi) \, d\phi \quad (b)$$

($r_p$ is not explicitly shown in the drawing).

The denominator of the equation (a) describing the centre of gravity $r_p$ of the plane is independent of the angle $\phi$ (except for measuring errors) so that, for determining the centre of rotation $r_c$, it may be written as:

$$r_c = \frac{\int_0^{2\pi} \int_{-r_{max}}^{r_{max}} Q(r,\phi) \, r \, dr \, d\phi}{\int_0^{2\pi} \int_{-r_{max}}^{r_{max}} Q(r,\phi) \, dr \, d\phi} \quad (c)$$

This integral can be determined numerically in that the integration range Q=0, . . . , $2\pi$; r= $-r_{max}$, . . . $+r_{max}$ is sampled at discrete points which are divided in a highly uniform manner.

In order to describe the integral (equation c) for discrete scanning points, the radius R, is defined by the numbering m of the detectors $D_m$ as:

$$r = R \sin[(m - m_c)\delta] \quad (d)$$

Figure 2:
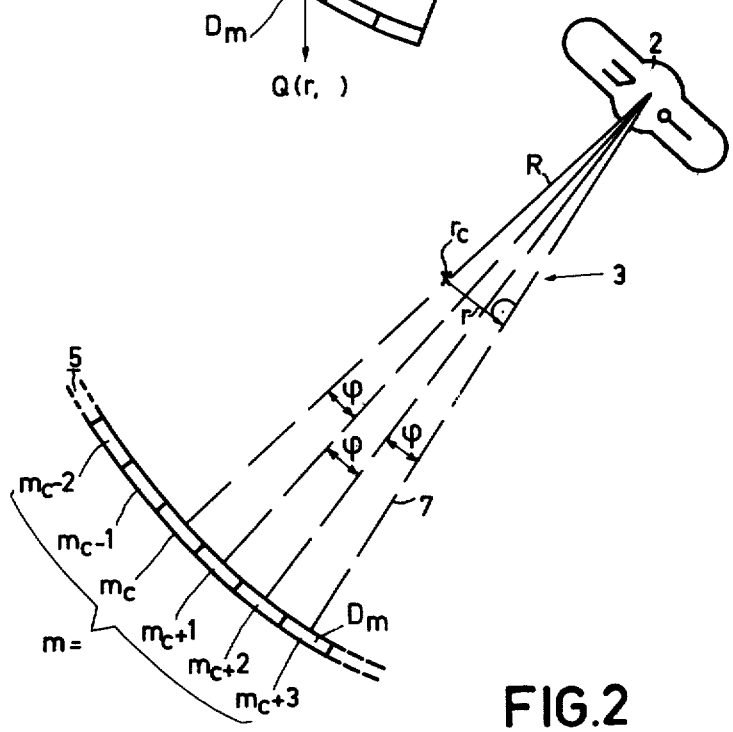
FIG. 2 represents a part of a radiation source which emits a fan-shaped beam.

To this end FIG. 2 shows a part of the fan-shaped radiation beam 3. The radiation source 2 and the centre of rotation $r_c$ (coordinate origin 8) are located at a distance R from each other. The angle enclosed by the centres of two adjacent detectors $D_m$ and X-ray source 2 is designated $\delta$. The index m represents the number of a detector $D_m$, m having the value m=1, . . . , M,) where M is the total number of detectors. The projection of the centre of rotation $r_c$ at the detector array 5 is indicated by an index $m_c$ corresponding to the index m. In contradistinction to m, $m_c$ may also be a fraction. The angle $\delta$ is now assumed to be constant. In most cases this requirement is met. If the angle $\delta$ is not constant, this should also be indicated by the detector number m. Thus, the individual detectors $D_m$ supply measuring data Q($r_m$, $\phi_n$) (the index n, which ranges from n=1 . . . N) indicating the position of the angle $\phi_n$ which represents the position of the central rays 7 in the polar coordinate system [r, $\phi$,] and N the total number of angles $\phi_n$.

Thus equation c may be written as an intermediate result:

$$\tilde{r}_c(\nu + 1) = \frac{r_c^{(\nu+1)}}{R} = \frac{\sum_{m=1}^{M} \tilde{Q}_m \sin[(m - m_c^{(\nu)})\delta] \cos[(m - m_c^{(\nu)})\delta]}{\sum_{m=1}^{M} \tilde{Q}_m \cos[(m - m_c^{(\nu)})\delta]} \quad (e)$$

In this equation $\nu$ is a counting index of an iteration, because the intermediate result $\tilde{r}_c^{(\nu+1)}$ depends on a previously obtained intermediate $\tilde{r}_c^{\nu}$.

The numerator of the intermediate result $\tilde{r}_c^{(\nu+1)}$ represents a first sum $S_1$ of intermediate values $Z^1_m$, which each time comprise an intermediate sum $Q_m$ where $$Q_m = \sum_{n=1}^{N} Q(r_m, \phi_n) \quad (f)$$

for the determination of which the detector signals $Q(r_m, \phi_n)$ of each time one detector $D_m$ for all directions $\phi_n$ are added. This intermediate sum is then multiplied by two functions $k_m = \sin[(m - m_c^{(\nu)})\delta]$ and $l_m = \cos[(m - m_c^{(\nu)})\delta]$ so as to obtain an intermediate value $Z^1_m$ (weighted). Subsequently, all intermediate values $Z^1_m$ for all detectors $D_m$ and all indexes m respectively are added so as to form a first sum $S_1$.

The second intermediate sum $S_2$ contained in the denominator of the intermediate result $\tilde{r}_c^{(\nu+1)}$ is formed accordingly. However, for an index m the intermediate sum $\tilde{Q}_m$ is only multiplied by the functional $l_m$.

In the case that the centre of rotation $r_c$ does not coincide with the coordinate origin 8, a correction value $\alpha$, where $$\alpha = \frac{1}{\delta} \cdot \tilde{r}_c^{(\nu+1)},$$

may be determined with the aid of the intermediate result $r_c^{(\nu+1)}$ which value is added to a first assumed index $m_c^{(\nu)}$, which describes the centre of rotation $r_c$, so as to determine an index $m_c^{(\nu)}$ which more accurately represents the centre of rotation $r_c$, in such a way that $$m_c^{(\nu+1)} = m_c^{(\nu)} + \frac{1}{\delta} \cdot \tilde{r}_c^{(\nu+1)} \quad (g)$$

As $m_c^{(\nu+1)}$ is an approximately linear function of $m_c^{(\nu)}$, two iteration steps will suffice to obtain a sufficient accuracy if the index $m_c^{(\hat{\nu}+1)}$ is linearly extrapolated as a function of the index $m_c^{(\nu)}$.

Two iteration steps then yield a final index $m_c$ which is representative of the centre of rotation $r_c$ with sufficient accuracy, where $$m_c = \frac{m_c^{(1)} m_c^{(1)} - m_c^{(0)} m_c^{(2)}}{2 m_c^{(1)} - m_c^{(0)} - m_c^{(2)}} \quad (h)$$

As zero approximation $m_c^{(0)}$ it is for example possible to write $m_c^{(0)} = M/2$.

Figure 3:
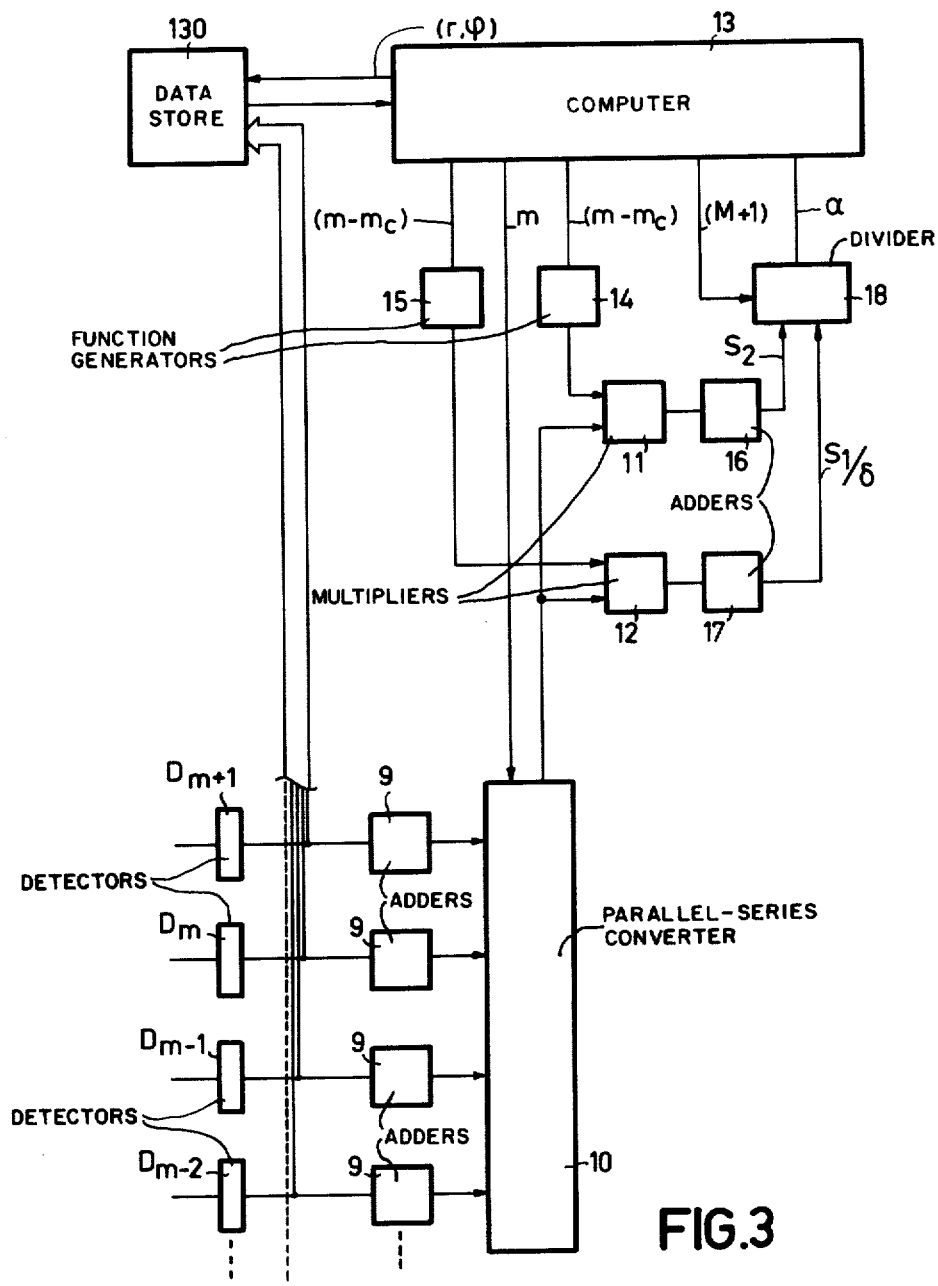
FIG. 3 is a block diagram of an apparatus for carrying out the method in accordance with the invention.

FIG. 3 shows a block diagram of an apparatus for carrying out the method in accordance with the invention. The detectors ..., $D_{m-1}$, $D_m$, $D_{m+1}$ supply measuring data $Q(r_m, \phi_n)$, which is stored in a data store 130, which is connected to a computer 13. Via an address line $(r, \phi)$ the computer 13 supplies addresses at which the measuring data $Q(r_m, \phi_n)$ are stored. By means of the computer 13 a radiation absorption distribution of the relevant slice of the body 4 (FIG. 1) may be reconstructed in a manner known per se, starting from the measuring data $Q(r_m, \phi_n)$, after the centre of rotation $r_c$ has been determined in accordance with a method according to the invention.

The measuring data $Q(r_m, \phi_n)$ from each detector $D_m$ are also applied to an adder circuit 9 associated with the detector $D_m$. The intermediate sum $Q_m$ of the measuring data obtained from the detector $D_m$ is stored in a parallel-series converter 10, which is connected to the adder circuits 9. By means of the computer 13 the intermediate sums $\tilde{Q}_m$ are called one by one via the line m and applied to the multipliers 11 and 12. The multipliers 11, 12 furthermore receive gonimetric functions $l_m$ and $(l_m \cdot k_m)/\delta$ via function generators 14 and 15 respectively, where $l_m = \cos[(m - m_c) \cdot \delta]$ and $k = \sin[(m - m_c) \cdot \delta]$. The value $(m - m_c)$, which determines the magnitude of the argument of the goniometric functions, is applied to the function generators 14 and 15 via the lines $(m - m_c)$ by the computer 13. The value $m_c$ is the detector number (which may be an integer or a fraction), which is fixed and preselected or which has been determined by a previous calculation of the centre of rotation $r_c$.

The products from the multipliers 11 and 12 are respectively applied to the adder circuits 16 and 17, which are identical to the adder circuits 9. After M multiplications and additions the value $$S_2 = \sum_{m=1}^{M} Q_m \cdot l_m$$

and the value $$S_1/\delta = \frac{1}{\delta} \sum_{m=1}^{M} \tilde{\phi}_m \cdot l_m \cdot k_m$$

are available on the outputs of the adder circuits 16 and 17 respectively.

The outputs of the adder circuits 16 and 17 are connected to a divider circuit 18, on whose output $\alpha$ the value $(r_c^{(\nu+1)})/\delta = S_1/(S_2 \cdot \delta)$ is obtained after a control pulse $M+1$, i.e. after all M multiplications and additions have been performed (see formula e). This value is equal to the value $\alpha$ with which the selected or precalculated value $m_c$ is to be corrected (see formula g), which value is applied to the computer 13.

What is claimed is:

1. A method for reconstructing an image of a radiation absorption distribution in a plane of a body by means of computerized tomography comprising, in combination, the steps of:

irradiating a plane of the body, from different directions in the plane, with penetrating radiation by rotating a radiation source which emits a fan-shaped beam of the radiation about a centre of rotation;

utilizing an array of radiation detectors to measure the attenuation of the beam of radiation in the body;

determining a first intermediate value $(Z_m^1)$ for each detector $(D_m)$, which first intermediate value is proportional to an intermediate sum $(\tilde{\phi}_m)$ obtained by summation of the measuring data $(Q(r_m, \tilde{\phi}_n))$ measured with the detector $(D_m)$ in the various directions $(\tilde{\phi}_n)$ and which intermediate sum further is proportional to goniometric functions $k_m$ and $l_m$, whose arguments are proportional to the difference between a variable detector number (m), which is representative of the position of the detector ($D_m$) in the array and a fixed preselected detector number ($m_c$) and to an angle ($\delta$) enclosed by the centres of two adjacent detectors in the array at the radiation source;

adding the first intermediate values from all of the detectors to form a first sum ($S_1$);

determining a second intermediate value for each detector number ($D_m$) ($Z^2{}_m$), which second value is proportional to the intermediate sum and the function $l_m$;

adding all of the second intermediate values to form a second sum ($S_2$);

dividing the first sum by the second sum to determine a third intermediate value ($\tilde{r}_c(\nu+1)$);

calculating a correction factor ($\alpha$), which is proportional to the third intermediate value and inversely proportional to the angle ($\delta$);

determining the position of the centre of roation from a number of the detector which is indicative of the position of the centre of rotation by adding the correction factor ($\alpha$) to a predetermined detector number; and reconstructing an image of the absorption distribution utilizing the methods of convolution and back-projection based on the aforesaid determined position of the centre.

2. A method for reconstructing an image of a radiation absorption distribution in a plane of a body by means of computerized tomography comprising, in combination, the steps of:

irradiating a plane of the body from different directions in the plane with penetrating radiation by rotating a radiation source which emits a fan-shaped beam of said radiation about a centre of rotation;

utilizing an array of radiation detectors to measure the attenuation of the beam of radiation in said body;

determining a first intermediate value ($\tilde{Z}_m{}^1$) for each direction ($\phi_n$), by summation of measuring data ($Q(r_m, \phi_n)$) measured with the detectors ($D_m$) in that direction and weighting the measuring data with goniometric functions $k_m$ and $l_m$ whose arguments are proportional to the difference between a variable detector number (m), which defines the position of a detector in the array and a fixed predetermined detector number ($m_c$), and to an angle ($\delta$) which is enclosed by the centres of two adjacent detectors at the radiation source;

adding the first intermediate values for all directions to form a first sum ($\tilde{S}_1$);

determining a second intermediate value ($Z^2{}_m$) for each direction by summation of the measuring data ($Q(r_m, \phi_n)$) measured by said detectors in that direction and weighting the sum with the goniometric function $l_m$;

adding all second intermediate values for all directions so to obtain a second sum ($S_2$);

determining a third intermediate value ($\tilde{r}_c{}^{(\nu+1)}$) by dividing the first sum by the second sum;

calculating a correction factor ($\alpha$) from the third intermediate value, which is proportional to the third intermediate result and inversely proportional to the the angle ($\delta$);

determining the position of the centre of rotation from a number of the detector which is indicative of the position of the centre of rotation by adding the correction factor ($\alpha$) to a predetermined detector number; and reconstructing an image of the absorption distribution utilizing the methods of convolution and back-projection based on the aforesaid determined position of the centre.

3. The method of claims 1 or 2 wherein the radiation is X-ray radiation.

4. Apparatus for reconstructing an image of the radiation absorption distribution in a plane of a body comprising, in combination:

a source for generating penetrating radiation;

a plurality of radiation detectors disposed in an array in the plane and connected for supplying measuring data which is a measure of the attenuation of radiation from the source which passes through the body in different directions in said plane;

data store means connected for the storage of the measuring data measured by the detectors;

computer means, connected to the data store means, for determining the radiation absorption in the plane by superposition of the measuring data;

first adder means, connected for receipt of the measuring data from the detectors, for formation of an intermediate sum therefrom;

parallel-series converter means connected to receive outputs from the adder means and to operate under the control of the computer means to sequentially render the intermediate sums at an output;

first and second multiplier means having first inputs, connected to receive the output of the parallel-series converter means, second inputs and outputs;

first and second function generator means connected to operate under the control of the computer and to furnish function outputs to the second inputs, respectively, of the multipliers;

second and third adder circuit means having inputs connected respectively to the outputs of the first and second multiplier means and having outputs;

dividing circuit means having first and second inputs which are connected, respectively, to the outputs of the second and third adder circuit means and having an output which is connected to supply data to the computer;

the first function generator means operating to generate a cosine function ($l_m$), whose argument is proportional to a value supplied by the computer and the second function generating means operating to supply a product ($l_m \cdot k_m$) of sine and cosine functions whose arguments are equal and proportional to the value supplied by the computer, the sum of the product from the first and second multipliers being applied to the dividing circuit means after all intermediate sums have been consecutively applied to the multipliers.

* * * * *